United States Patent
Needleman

(10) Patent No.: US 8,790,710 B1
(45) Date of Patent: Jul. 29, 2014

(54) TOPICAL COMPOSITION COMPRISING UMBILICAL CORD BLOOD SERUM

(75) Inventor: Alvin Needleman, Las Vegas, NV (US)

(73) Assignee: Novo Solutions, MD, L.L.C., Paradise Valley, AZ (US)

( * ) Notice: Subject to any disclaimer, the term of this patent is extended or adjusted under 35 U.S.C. 154(b) by 394 days.

(21) Appl. No.: 12/836,168

(22) Filed: Jul. 14, 2010

Related U.S. Application Data

(60) Provisional application No. 61/278,040, filed on Oct. 2, 2009.

(51) Int. Cl.
*A61K 35/16* (2006.01)
(52) U.S. Cl.
USPC ........................................ 424/531

(58) Field of Classification Search
None
See application file for complete search history.

(56) References Cited

U.S. PATENT DOCUMENTS

| | | | |
|---|---|---|---|
| 2003/0232432 A1* | 12/2003 | Bhat | 435/366 |
| 2007/0077232 A1 | 4/2007 | Naughton et al. | |
| 2008/0132803 A1 | 6/2008 | Friedlander | |
| 2011/0177015 A1* | 7/2011 | Friedlander | 424/70.1 |

FOREIGN PATENT DOCUMENTS

| | | |
|---|---|---|
| WO | WO 2007/099534 | 9/2007 |
| WO | WO 2010/038232 | 4/2010 |

* cited by examiner

*Primary Examiner* — James Martinell
(74) *Attorney, Agent, or Firm* — Stinson Leonard Street LLP

(57) ABSTRACT

Cosmetic compositions comprising umbilical cord blood serum and methods of using such compositions to impart anti-aging benefits to the skin are disclosed.

10 Claims, No Drawings

TOPICAL COMPOSITION COMPRISING UMBILICAL CORD BLOOD SERUM

CROSS-REFERENCE TO RELATED APPLICATIONS

This application is based on and claims priority to U.S. Provisional Application Ser. No. 61/278,040, filed on Oct. 2, 2009 which is incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to the field of cosmetics. It relates more particularly to novel cosmetic compositions comprising umbilical cord blood serum, and to novel uses of such compositions in the field of cosmetics, especially as an anti-aging and anti-wrinkle formulation.

2. Description of Related Art

The gradual development of facial wrinkles, whether fine surface lines or deeper creases and folds, is an early sign of accumulated skin damage and skin aging, which may be intrinsic and/or caused or accelerated by external factors. For example, premature aging and wrinkling of the skin may be accelerated by excessive exposure to the sun and other damaging elements, overactive facial expression muscles, frequent use of tobacco products, poor nutrition, or skin disorders. Fine surface wrinkles that progress to deeper creases, deepening facial expression due to repeated skin folding, and deep folds which develop with one's maturity are visible changes which may combine to portray a less desirable appearance.

Various attempts at anti-aging skin care compositions have used botanicals, antioxidants, and biopeptides, among other things. Several invasive techniques are available in which substances are injected or implanted in the area of the skin which either temporarily weaken the muscles or act as skin volume fillers. However, invasive techniques are often risky and require the supervision or assistance of a physician, which can be inconvenient and costly, and non-invasive treatments have historically met with only minimal success. Regardless of the cause of facial creases or folds, safe and effective treatments for reduction or elimination of these problems have been exceedingly difficult to achieve. Thus, there remains a need for new and improved topical skin care compositions that are useful as an anti-aging composition.

BRIEF SUMMARY OF THE INVENTION

The present invention is directed to novel skin care composition comprising an effective amount of umbilical cord blood serum for topical application to the human skin. The compositions are useful for imparting a so-called "anti-aging" benefits to the skin.

In one aspect, the umbilical cord blood serum is present in an amount from about 0.0001 wt % to about 90 wt % of the composition, more preferably between about 0.01 wt % to about 25 wt %, and still more preferably about 0.01 wt % to about 15 wt %, and still more preferably about 0.1 wt % to 3.0 wt %.

In still another aspect, the composition is formulated with other cosmetic actives and excipients. For example, in one exemplary aspect, the skin care composition comprises a peptide selected from the group consisting of the tyr-arg, acetyl hexapeptide-3, palmitoyl oligopeptide, palmitoyl tetrapeptide-7, and mixtures thereof. In another exemplary aspect, the skin care composition comprises a biological additive selected from the group consisting of *Juglans regia, Centella asiatica, Pyrus germanica* extract, and mixtures thereof. In another exemplary aspect, the skin care composition comprises a biological additive selected from the group consisting of *Undaria pinnatifida* and *Stevia rebaudiana* Bertoni, and mixtures thereof. In still another exemplary aspect, the skin care composition comprises one or more phosphospholipids, such as one selected from the group consisting of phosphatidyl choline, phosphatidyl ethanolamine, phosphatidyl serine, phosphatidyl inositol, diphosphatidyl glycerol, and mixtures thereof. In still another exemplary aspect, the skin care composition comprises one or more preservatives, such as sodium benzoate, potassium sorbate, or methyl and/or propyl paraben. In yet another exemplary aspect, the skin care composition comprises one or more penetration enhancers, such as dimethyl isosorbide, polar aprotic solvent dimethyl sulfoxide, and diethyl-glycol-monoethylether. In still another exemplary aspect, the skin care composition comprises one or more neutralizing agents, such as triethanolamine and/or polyamino carboxylic acid ethylenediaminetetraacetate. In yet another exemplary aspect, the skin care composition comprises one or more hyaluronans. In still a further exemplary embodiment, the skin care composition comprises one or more skin-conditioning emollients, such as those selected from the group jojoba oil, almond oil, capric/caprylic triglyceride, and mixtures thereof. In yet another exemplary aspect, the skin care composition comprises one or more surfactants, such as myristamidopropyl PG-dimonium chloride phosphate. In yet another aspect, the skin care composition comprises one or more spreading agents, such as PPG-3 benzyl ether myristate is used as a spreading agent. In another aspect, the skin care composition comprises one or more gelling agents, such as carbomer and/or monomers of hexyl cellulose.

In another aspect, the skin care composition comprises about 0.1 to about 0.35 wt % umbilical cord blood serum, about 3 to 5 wt % palmitoyl oligopeptide, about 3 to about 5 wt % palmitoyl tetrapeptide-7. In still yet another aspect, the skin care composition comprises about 2 to about 3 wt % of the dipeptide tyr-arg and about 0.5 to 1.5 wt % acetyl hexapeptide-3.

Yet in another aspect, the skin care composition comprises about 0.5 to about 1.2 wt % phosphatidyl choline, about 0.5 to about 1.5 wt % hyaluronans, and 0.01 to 0.085 wt % of a preservative selected from the group consisting of sodium benzoate and potassium sorbate, or mixtures thereof. In yet another aspect, the skin care composition comprises *juglans regia, centella asiatica, pyrus germanica, Undaria pinnatifida,* and *Stevia rebaudiana* Bertoni.

The present invention is also directed to a method for imparting an anti-aging benefit to human skin comprising: topically applying to the skin of an individual in need thereof any of the foregoing compositions. In a preferred aspect, application of the composition to the skin results in improved procollagen and glycosaminoglycans content.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The present invention is directed to novel skin care compositions for topical application to the human skin comprising an effective amount of umbilical cord blood serum. The umbilical cord blood serum is present in an effective amount to treat, reverse, ameliorate, and/or repair signs of skin damage or skin aging. Such benefits may include without limitation, the following: (a) treatment, reduction, and/or prevention of fine lines or wrinkles, (b) improvement in skin thickness, plumpness, and/or tautness; (c) improvement in skin suppleness and/or softness; (d) improvement in skin tone, radiance, and/or clarity; (e) improvement in procollagen and/or collagen production; (f) improvement in maintenance and remodeling of elastin; (g) improvement in skin texture and/or promotion of retexturization; (h) improvement in skin barrier repair and/or function; (i) improvement in appearance of skin contours; (j) restoration of skin luster and/or brightness; (k) replenishment of essential nutrients and/or constituents in the skin; (l) improvement of skin appearance decreased by aging; (m) improvement in skin moisturization and/or hydration; (n) increase in and/or preventing loss of skin elasticity and/or resiliency; (o) treatment, reduction, and/or prevention of skin sagging; and/or (p) treatment, reduction, and/or prevention of discoloration of skin.

In practice, the compositions of the invention are applied to skin in need of treatment. That is, the composition is applied to skin which suffers from a deficiency or loss in any of the foregoing attributes or which would otherwise benefit from improvement in any of the foregoing skin attributes. As such, in certain preferred embodiments the compositions and methods of the invention are directed to the prevention, treatment, and/or amelioration of fine lines and/or wrinkles in the skin. In one exemplary preferred case, the compositions are applied to skin in need of treatment, by which is meant skin having wrinkles and/or fine lines. Preferably, the compositions are applied directly to the fine lines and/or wrinkles (which may be the entire face and/or neck area, or a portion thereof). The compositions and methods are suitable for treating fine lines and/or wrinkles on any surface of the skin, including without limitation, the skin of the face, neck, and/or hands.

The compositions of the present invention may be applied as needed to the skin. The composition can be applied periodically, e.g., daily, twice daily, weekly, or several times a week. The composition is generally applied for a duration of one week to indefinitely, such often will be applied for a period of 1, 2, 3, 4, 5, 6, or more months. The duration of application can also be applied for an indefinite time period, if desired. It will be appreciated that the results discussed herein will depend upon the amount frequency, and duration of application, with highest amounts and more frequent applications providing accordingly faster results. The skin-care compositions are applied daily preferably for at least four weeks, and more preferably at least eight weeks, by which an effect upon the appearance of skin should be observed. Application may be continued as long as desired to maintain the condition of the skin.

In addition, it is also contemplated that the compositions of the present invention may be applied to normal healthy skin, and may improve the brilliance, smoothness, radiance, and/or elasticity of the normal skin. Thus, in another aspect, the compositions are applied to the skin of the face, neck, and or hands of a patient having normal skin. It is anticipated that the surface characteristics of the unwrinkled, unsagging skin may be improved.

The compositions according to the invention can be formulated in a variety of forms for topical application. Typically, the compositions will comprise from about 0.0001 wt % to about 90 wt % of umbilical cord blood serum, and preferably will comprise from about 0.001 wt % to about 25 wt %, more preferably from about 0.01 wt % to about 10 wt %, and still more preferably about 0.05 wt % to about 5 wt % of umbilical cord blood serum. Within the more preferred range, the composition may comprise umbilical cord blood serum within a 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1.0 wt % of the total composition. As an example, the compositions will comprise an effective amount of umbilical cord blood serum, by which is meant an amount sufficient improve procollagen and/or glycosaminoglycans, for example as discussed in the Examples. An "effective amount" in the context of umbilical cord blood serum includes one that provides a particular anti-aging benefit to the skin and refers to the amount required to provide a clinically measurable improvement in the particular manifestation of skin aging when applied for a time sufficient to provide a clinically measurable improvement in the particular manifestation of skin aging.

The composition of the present invention may be formulated in a variety of product forms, such as, for example, a lotion, cream, serum, spray, aerosol, cake, ointment, essence, emulsion, gel, paste, patch, pencil, towelette, mask, stick, foam, concentrate, and the like, particularly for topical administration. Preferably the composition is formulated as a lotion, cream, ointment, serum, or gel.

The compositions of the present invention may include a cosmetically acceptable vehicle. Such vehicles may take the form of any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives, stabilizers, pharmaceutical agents, photostabilizing agents, neutralizers, and mixtures thereof. In addition to the foregoing, the cosmetic compositions of the invention may contain any other compound for the treatment of skin disorders.

As used herein, "topical application" means directly laying on or spreading on outer skin.

As used herein, "cosmetically acceptable" means that drugs, medicaments, botanicals, chemicals, or inert ingredients which the term describes are suitable for use in contact with the tissues of humans and lower animals without undue toxicity, incompatibility, instability, irritation, allergic response, and the like, commensurate with a reasonable benefit/risk ratio. Cosmetically acceptable vehicles must be of sufficiently high purity and sufficiently low toxicity to render them suitable for administration to the human or lower animal being treated.

As used herein, "comprising" means that other steps and other ingredients which do not affect the end result can be added. This term encompasses the terms "consisting of" and "consisting essentially of."

The term "sagging" as used herein means the laxity, slackness, or the like condition of skin that occurs as a result of loss of, damage to, alterations to, and/or abnormalities in dermal elastin and includes the age-related loss of adhesive plaque at the dermal-epidermal junction.

The terms "smoothing" and "softening" as used herein mean altering the surface of the keratinous tissue such that its tactile feel is improved. "Signs of skin aging" include, but are not limited to, all outwardly visible or tactilely perceptible manifestations as well as any other macro or micro effects due to skin aging. Such signs may be induced or caused by intrinsic factors or extrinsic factors, e.g., chronological aging and/or environmental damage. These signs may result from processes that include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including under eye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

The term "umbilical cord blood" or "cord blood" generally refers to blood obtained from a neonate or fetus, most preferably a neonate and preferably refers to blood which is obtained from the umbilical cord or placenta of newborns. The use of cord or placental blood is advantageous because it can be obtained relatively easily and without trauma to the donor. Cord blood is preferably obtained by direct drainage from the umbilical vein of a discarded placenta.

The term "umbilical cord blood serum" or "cord serum" generally refers to umbilical cord blood in which the cells have been removed so that the cord serum is substantially free of whole cells.

The term "wrinkle" or "wrinkling" includes both fine wrinkling and coarse wrinkling. Fine wrinkling or fine lines refers to superficial lines and wrinkles on the skin surface. Coarse wrinkling refers to deep furrows, particularly deep lines/wrinkles on the face and around the eyes, including of expression lines such as frown lines and wrinkles, forehead lines and wrinkles, crow's feet lines and wrinkles, nasolabial fold, and marionette lines and wrinkles. Forehead lines and wrinkles refer to superficial lines and/or deep furrows on skin of the forehead. Crow's feet lines and wrinkles refer to superficial lines and/or deep furrows on skin around the eye area. Marionette lines and wrinkles refer to superficial lines and/or deep furrows on skin around the mouth. Wrinkles can be assessed for number, length, and depth of the lines.

Umbilical Cord Blood Serum

The umbilical cord blood serum used in the compositions of the present invention is typically prepared in the following manner. First, umbilical cord blood is collected at the time to birth from pre-screened mothers for infectious disease causing organisms, such as HIV 1 and 2, Hbs and HCV and sexually transmitted diseases. The collection is made after the baby is separated from the clamped cord, and therefore there is no harm to the baby. Blood is collected from an umbilical vein using the conventional blood bag containing no anticoagulants. The needle of the bag is inserted into the vein and blood is allowed to flow into the blood bag. A good collection can average 40 ml and may exceed 100 ml. This blood is now allowed to clot at room temperature and transported to the processing area, which is a cGMP clean room. The clotting process is allowed to take place from 8-16 hours. The blood is then centrifuged at 1000 g in a blood bag centrifuge and the clear serum is collected into sterile containers. The cord serum is tested for sterility by microbiological assays for aerobic or anaerobic microorganisms. The complement is inactivated by keeping the cord serum at about 56° C. for ½ hour. The serum is then aliquoted into 50 ml sterile vials and capped and frozen at about −70° C. for future use in the compositions of the present invention. Suitable cord serum is commercially available from Cryobanks Laboratories (Allamonte Springs, Fla.), and Morphogenesis Laboratories, St. Josephs Childrens Hospital (Tampa, Fla.).

Other Optional Components

The cosmetic compositions of the present invention preferably include one or more bioactive peptides, including but not limited to, dipeptides, tripeptides, tetrapeptides, pentapeptides, and hexapeptides, and derivatives thereof. The peptides are provided in the compositions of the present invention in amounts that are safe and effective. As used herein, "peptides" refers to both the naturally occurring peptides and synthesized peptides. Also useful herein are naturally occurring and commercially available compositions that contain peptides. The peptides used in the present invention may include neuropeptides as well as so-called charge-coupled peptides.

Suitable dipeptides for use herein include carnosine (beta-ala-his) and tyr-arg. Suitable tripeptides for use herein include gly-his-lys, arg-lys-arg, and his-gly-gly. Preferred tripeptides and derivatives thereof include palmitoyl oligopeptide (palmitoyl-gly-his-lys); Peptide CK (arg-lys-arg); Peptide CK+ (ac-arg-lys-arg-$NH_2$); and a copper derivative of his-gly-gly sold commercially as lamin, from Sigma (St. Louis, Mo.). Suitable tetrapeptides for use herein include Peptide E, arg-ser-arg-lys (SEQ ID NO: 1); palmitoyl tetrapeptide-3/7 (palmitoyl-gly-gln-pro-arg (SEQ ID NO: 2)). Suitable pentapeptides for use herein include lys-thr-thr-lys-ser (SEQ ID NO: 3), palmitoyl-lys-thr-thr-lys-ser (SEQ ID NO: 4). Suitable hexapeptides include acetyl hexapeptide-3 (Ac-Glu-Glu-Met-Gln-Arg-Arg (SEQ ID NO: 5)). When included in the present compositions, peptides are typically present in amounts of from about 0.01 wt % to about 10 wt %, or from about 0.1 wt % to about 6.0 wt %, or from about 1.0% to about 0.5%, by weight of the composition.

In one aspect, the cosmetic compositions of the present invention include one or more dipeptides. The preferred dipeptide comprises tyr-arg. In a preferred aspect, the tyrosine-arginine dipeptide is acetylated to make it more lipophilic, more stable, and bio-available on a cutaneous level. Acetyl tyrosine-arginine-1 cetyl ester stimulates the synthesis of the messenger neuropeptides of muscular relaxation and inhibits the synthesis of the messenger mediators of muscular contraction. The compositions of the invention preferably comprise about 0.001 to 5.0 wt % of the dipeptide, especially tyr-arg. In a preferred aspect, the compositions comprise about 2.0 to about 3.0 wt % of the dipeptide.

In one aspect, the cosmetic composition of the present invention includes one or more tripeptides and tetrapeptides. In a preferred embodiment, the cosmetic composition includes the commercially available product known as MATRIXL 3000® (Sederma Corp., France), which includes both palmitoyl oligopeptide and palmitoyl tetrapeptide-7. The compositions of the invention preferably comprise about palmitoyl oligopeptide and palmitoyl tetrapeptide-7 in a combined amount of about 0.001 to about 10 wt %. In a preferred aspect, the compositions comprise about 3.0 to about 5.0 wt % palmitoyl oligopeptide and palmitoyl tetrapeptide-7.

In one aspect, the cosmetic compositions of the present invention include one or more hexapeptides. The preferred hexapeptide used in the compositions of the invention is acetyl hexapeptide-3. The peptide may be purchased from Lipotec under the tradename Argireline® in either the powder or solution form. The powder form appears as a white to off-white powder. The compositions of the invention preferably comprise about 0.001 to about 5.0 wt % acetyl hexapeptide-3. In a preferred aspect, the compositions comprise about 0.5 to about 1.5 wt % acetyl hexapeptide-3.

In one aspect, the cosmetic compositions of the present invention include one or more biological additives, such as botanicals or herbals. As used herein, the term "biological additive" indicates any compound obtained from a natural source, including plants, animals, bacteria, and yeast, which has a medicinal or otherwise beneficial effect when topically applied to the skin. Examples of biological additives include oil of *Melaleuca alternifolia*, oil of *Lavandula angustifolia*, *Carica papaya* extract, *Echinacea angustifolia* extract, *Mimosa tenuiflora* extract, *Hydrocotyl* (*centella*) *asiatica* extract, *gingko biloba* extract, oil of *Melaleuca alternifolia* (tea tree oil), *Matricaria chamomila* (chamomile) extract, *Hypericum perforatum* extract, *Aloe barbedensis* extract, and the like. The biological sources for "biological additive" may also include, but are not limited to the following: *Aloe Vera, Aloe Barbedensis; Arnica, Arnica* Montana; Bladderwrack (seaweed), *Fucus Vesciculosis*; Seaweed, *Undaria pinnatifida*; Birch, *Betula Alba (Pendula)*; Chamomile, *Matricaria Chamomila (Chamomila Recutita)*; Marsh Mallow, *Althea Officinalis*; Meadow Sweet, Spirea Ulmaria (*Filipendula*); Mint/Lemon Balm, *Melissa Officinalis*; Mimosa, *Mimosa Tenuflora*; Myrrh Tincture, *Commiphor Myrrha*; Neem, Melia Azadirachta; Nettle (stinging), *Urtica Dioica*; Papaya, *Carica Papaya*; Propolis (bee glue), *Propolis Cera*; Raspberry, *Rubis Idaeus*; Red Poppy, *Papaver Rhoeas*; Rose Hip (dog rose), *Rosa Carima*; Rosemary, *Rosemarinus Officinalis*; Sage, *Salvia Officinalis*; St. Johns Wort, *Hypericum Perforatum*; Strawberry, *Fragaria Vesca*; Thea Sinensis (green tea), *Camelia Sinensis*; Walnut, *Juglans Regia*; Witchhazel (dist/extr), *Hamamelis Virginiana*; Yarrow, *Achillea Millefolium*; Wild Yam, *Dioscorea Villosa*; Hawthorn, *Crataegus Monogina/Oxyantha*; Herma (black/rod), *Lawsoma Ehemus*; Hops, *Humulus Lupulus*; Horse Chestnut, *Aesculus Hippocastanum*; Horse Tail, *Equisitum Arvense*; Ivy, *Hedera Helix*; Linden/Lime Tree Blossoms, *Tilia Argentea Cordata*; Madder, *Rubia Tinctorum*; Marigold, *Calendula Officinalis; Centella Asiatica, Centella Asiatica* Urban (hydrocotyl Asiatica); Carrot (roots), *Daucus Carota*; Comfrey (Allantoine), *Symphytum Officinale*; Coneflower (Echinacea), *Echinacea Angustifolia*; Cucumber, *Cucumis Sativus (Frucus Cucumis)*; Fenugreek, *Trigonella Foenum Greacum*; Gingko, *Gingko Biloba*; Ginseng, *Panax Ginseng*; Great Burdock, *Radix Bardanea/Arctium Lappa*; Tea Tree Oil, Oil of *Melaleuca Alternifolia*; Colts Foot, *Tussilago Farfara*; Clover, *Trifolium Pratense*; Speedwell, *Veronica Officinalis*; Medlar, *Pyrus Germanica*.

In another aspect, the biological additive may be those selected from the group consisting of plants such as *Angelica keiskei*, adzuki bean, avocado, hydrangea, *Gynostemma pentaphyllum*, Aruteka, arnica, almond, aloe, apricot, nettle, iris, fennel, turmeric, Eijitsu, Scutellariae radix, Amur cork tree, goldthread, barley, gumbo, Saint-John's-wort, dead nettle, ononisu, watercress, persimmon, the root of kudzu, *Valeriana fauriei*, birch, cattail, chamomile, chamomilla, oats, licorice, raspberry, kiwi, cucumber, apricot, coconut, cape jasmine, *Sasa albo-marginata*, a walnut, cinnamon, mulberry, gunjo, gentian, cranesbill, burdock, sesame, wheat, rice, *Camellia sasangua*, saffron, hawthorn, Japanese pepper tree, mushroom, *Rehmannia clutinosa*, prop root, beefsteak plant, Japanese linden, *Filipendula multijuga*, peony, ginger, calamus, white birch, Japanese honeysuckle, field horsetail, *Stevia rebaudiana* Bertoni, western ivy, western hawthorn, elder, needle juniper, milfoil, mint, sage, common mallow, *Cnidium officinale*, Japanese green gentian, soybean, daiso, thyme, tea plant, clove, dried orange peel, evening primrose, camellia, *Centella asiatica*, English walnut, *Angelica acutiloba*, pot marigold, ginseng, orange peel, corn, *Houttuynia cordata*, tomato, carrot, garlic, wild rose, malt, parsley, rye, adlay, Japanese mint, papaya, hamamelis, rose, white cedar, sunflower, loquat, butterbur, dandelion, grape, placenta, hazelnut, dishcloth gourd, safflower, bo tree, peony, hop, macadamia nut, pine, horse chestnut, melissa, melilot, peach, malt, Rodger's bronze leaf, palm, eucalyptus, creeping saxifrage, lily, Yokuninin, mugwort, rye, peanut, lavender, apple, litchi, lettuce, lemon, Chinese milk vetch, rosemary, camomile, agrimony, Japanese catalpa, hiba arborvitae, Horutso, *Isodon japonicus* Hara, jijitsu, senkishi, chickweed, duckweed, mugwort, ginkgo, Chinese bellflower, chrysanthemum, soapberry and weeping golden bell.

In one exemplary aspect, the biological additive comprises PHYTOTAL FM (Croda Singapore) in an amount of about 0.5 to about 6.0 wt % of the composition, preferably about 3.5 to about 5.5 wt % of the composition. PHYTOTAL FM comprises glycerin, butylene glycol, *juglans regia* leaf extract, *Juglans regia* shell extract, *Centella asiatica* extract, *Pyrus germanica* extract, and lecithin. In another exemplary aspect, the cosmetic compositions of the present invention comprise about 0.1 to about 6.0 wt %, preferably about 2.0 to about 4.0 wt % seaweed, *Undaria pinnatifida*. In still another exemplary aspect, the cosmetic compositions of the present invention comprise *Stevia rebaudiana* Bertoni in an amount of about 0.1 to about 6.0 wt %, with about 2.0 to about 4.0 wt % being most preferred.

In general, these extracts can be obtained by grinding the whole of the respective plants or one or more of their parts (hereinafter referred to as "stocks" such as leaves, bark, roots, branches, seeds or fruits or nuts, and flowers or blossoms after drying them or without drying them, and then extracting them either with a solvent or by means of an extractor such as a Soxhlet's extractor at ordinary temperature or an elevated temperature. No particular limitation is imposed on the solvent used here. However, examples thereof include known solvents, such as water, primary alcohols such as methyl alcohol and ethyl alcohol, liquid polyhydric alcohols such as propylene glycol and 1,3-butylene glycol, lower alkyl esters such as ethyl acetate, hydrocarbons such as benzene and hexane, ethyl ether; and acetone. These solvents may be used either singly or in any combination thereof.

The cosmetic compositions also preferably includes one or more lipids, preferably one or more phosphospholipids. Examples of three classes of phospholipids are phosphoglycerides, lysophosphoglycerides, and sphingomyelins. Examples of phosphoglycerides include phosphatidyl choline, phosphatidyl ethanolamine, phosphatidyl serine, phosphatidyl inositol, diphosphatidyl glycerol, and mixtures thereof. The most preferred phosphoglycerides include phosphatidyl choline and lecithin, particularly soybean lecithin, which comprises a mixture of some of the above examples of specific phosphoglycerides. Examples of lysophosphoglycerides includes: lysophosphatidyl choline, lysophosphatidyl ethanolamine, lysophosphatidyl serine, lysophosphatidyl inositol, and mixtures thereof. The lipids (e.g., phosphatidyl choline) preferably comprise about 0.1 to about 6.0 wt % of the cosmetic composition, with about 0.5 to about 1.2 wt % being most preferred.

The cosmetic compositions of the present invention may also comprise one or more preservatives. Suitable traditional preservatives for compositions of this invention are alkyl esters of para-hydroxybenzoic acid. Other preservatives include hydantoin derivatives such as 1,3-bis(hydroxymethyl)-5,5-dimethylhydantoin, propionate salts, and a variety of quaternary ammonium compounds such as benzalkonium chloride, quaternium 15, benzethonium chloride, and methylbenzethonium chloride. Cosmetic chemists are familiar with appropriate preservatives and routinely choose them to satisfy the preservative challenge test and to provide product stability. Particularly preferred preservatives are disodium EDTA, phenoxyethanol, methyl paraben, propyl paraben, imidazolidinyl urea, sodium dehydroacetate, sodium benzoate, potassium sorbate, and benzyl alcohol. The preservatives should be selected having regard for the use of the composition and possible incompatibilities between the preservatives and other ingredients in the emulsion. The preservatives preferably are employed in amounts ranging from about 0.001 wt % to about 5 wt %, more preferably from about 0.01 wt % to about 2.5 wt %, and most preferably from about 0.01 wt % to about 1 wt %, by weight of the composition.

The cosmetic compositions of the present invention may also comprise one or more penetration enhancers. As used herein, a penetration enhancer is a material capable of aiding the penetration of the active agents into the skin. Examples of penetration enhancers include, but are not limited to, dimethyl isosorbide, dimethyl sulfoxide, and diethyl-glycol-monoethylether. The penetration enhances typically comprise about 0.5 to about 5 wt % of the composition, preferably about 1.0 to 3.0 wt %.

In still another aspect, the compositions of the present invention may further comprise one or more neutralizing gents or pH adjusters, which may be used to adjust the pH of the compositions. The term "neutralizing agent," as used herein, refers to a material that may be used to modify the pH of the present compositions, for example, from an acidic pH to a more basic pH, or from a basic pH to a more acidic pH. Components of the present compositions, such as certain of the thickening agents, may be acidic, and may be preferably neutralized to achieve the desired thickening effect. Accordingly, the neutralizing agents are preferably those materials which may be used to modify the pH of the present compositions from an acidic pH to a more basic pH.

A wide variety of neutralizing agents are known to those skilled in the art and may be used in the practice of the present invention. Exemplary neutralizing agents include, for example, ammonium hydroxide, arginine, 2-amino-2-methyl-1-propanol (AMP-95 (Angus)), dimethanolamine, dibutanolamine, diisobutanolamine, tributanolamine, triisobutanolamine, tri-sec-butanolamine, tripropylamine, ethanolamine, diethanolamine, triethanolamine, PEG-15 cocamine, diisopropanolamine, methylethanolamine, diisopropylamine, dipropylenetriamine, tromethamine, isopropylamine ethylene diamine, triisopropanolamine, tetrahydroxypropyl ethylenediamine, trimethamine, 2-aminobutanol, aminoethyl propanediol, aminomethyl propanediol, aminomethyl propanol, sodium hydroxide, potassium hydroxide, and mixtures thereof. Most preferably, the preferably, the neutralizing agent triethanolamine. The amount of neutralizing agent in the cosmetic composition is preferably about 1.0 to about 6.0 wt % with about 0.75 to about 1.5 wt % being most preferred.

In one aspect, the cosmetic compositions of the present invention include one or more hyaluronans. Preferably, the hyaluronan is present in the form of hyaluronic acid or salt thereof or a homologue, analogue, derivative, complex, ester, fragment and subunit of hyaluronic acid. More preferably, the hyaluronic acid in the form of sodium hyaluronate and is of cosmetic grade and has a molecular weight range of 5 kDa to 3 MDa. The compositions of the invention preferably comprise about 0.01 to about 4.0 wt % hyaluronan (in the form of sodium hyaluronate). In a preferred aspect, the compositions comprise about 0.5 to about 1.5 wt % hyaluronan (in the form of sodium hyaluronate).

In one aspect, the cosmetic compositions of the present invention include one or more skin-conditioning emollients. The emollient functions as a softener to help the composition give a desirable feel on the skin. Useful emollients include, but are not limited to fatty bodies liquid at ambient temperature, such as esters, mineral oils, animal oils, vegetable oil, synthetic oils, and silicone oils. Examples of useful esters include, but are not limited to, isononyl isononanoate, octyl palmitate, cetyl lactate, pentaerythrityl tetraoctanoate, tridecyl octanoate, tridecyl behenate, isopropyl jojobate and jojoba alcohols, butyloctyl salicylate, polyglyceryl-3 diisostearate, squalane, tridecyl trimellitate, tridecyl stearate, and neopentylglycol dicaprylate/dicaprate. Examples of useful oils include, but are not limited to, petrolatum oil, liquid lanolin, arara oil, sesame oil, macadamia oil, almond oil, jojoba oil, silicone oils such as phenyl trimethicone and dimethicone, and synthetic triglycerides such as capric/caprylic triglyceride and hydrogenated cocoglycerides. The emollient(s) can be present in the present invention in an amount about 0.1 wt % to about 6 wt %. In an exemplary aspect, the cosmetic composition comprises about 0.1 to about 6 wt %, and more preferably about 0.75 to 1.5 capric/caprylic triglycerides. In another aspect, the cosmetic composition comprises about 0.1 to 6 wt %, and more preferably about 0.3 wt % to about 0.7 wt % almond oil. In an another aspect, the cosmetic composition comprises about 0.1 to about 6 wt %, and more preferably about 0.75 wt % to about 1.5 wt % jojoba oil.

In still another aspect, the cosmetic compositions may contain one or more surfactants. Exemplary surfactants are disclosed in Harrison et al. U.S. Pat. No. 6,642,194, which is incorporated by reference. A preferred surfactant is myristamidopropyl PG-dimonium chloride phosphate and it has cationic properties and is also a preservative booster. Another preferred surfactant are the betaines, preferably alkylamidoalkylbetaines, such cocoamidopropylbetaine.

Other agents that may form part of the cosmetically acceptable vehicle of the cosmetic formulation include carbomers, propylene glycol, butylene glycol, dipropylene glycol, glycerin, glycereth-18 ethylhexanoate, glycereth-18, betaine, diglycerin, glycol, inositol, meadowfoamamidopropyl betaine, ethyl alcohol, isopropyl alcohol, polyethylene glycol with varied molecular weights, sorbitol, xylitol, urea, tripropylene glycol, sodium PCA, glycereth-7 glycolate, diglycereth-7 malate, 2,3-butanediol, propanediol, xylose, almond oil PEG-6 esters, apricot kernel oil PEG-6 esters, argan oil PEG-8 esters, and argan oil polyglyceryl-6 esters. Other vehicle agents include PEG-3 dimethicone, PEG/PPG-20/23 dimethicone, PEG-8 dimethicone, cyclomethicone, dimethicone, cetyl dimethicone, caprylyl methicone, ethyl trisiloxane, trimethylsiloxyamodimethicone, stearyl dimethicone, silicones with polypropylene glycol functionality such as PPG-12 dimethicone; silicones with polyethylene glycol functionality such as PEG-8 trisiloxane, PEG-10 dimethicone and silicones which combine both functionalities in varying ratios such as PEG/PPG-5/3 trisiloxane, PEG/PPG-8/26 dimethicone, PEG/PPG-20/15 dimethicone, bis-PEG-4 dimethicone, bis-PEG-12 dimethicone, bis-PEG/PPG-14/14 dimethicone, bis-PEG/PPG-18/6 dimethicone, bis-PEG/PPG-20/20 dimethicone, butylene glycol behenate, butylene glycol diisononanoate, butylene glycol laurate, butylene glycol myristate, butylene glycol oleate, butylene glycol palmitate, butylene glycol stearate, butyl isostearate, butyl myristate, butyloctyl behenate, butyloctyl benzoate, butyloctyl cetearate, butyloctyl palmitate, butyl oleate, butyl stearate C14-15 alcohols, C18-28 alkyl acetate, C12-15 alkyl benzoate, C16-17 alkyl benzoate, C30-45 alkyl cetearyl dimethicone crosspolymer, C32 alkyl dimethicone, C30-45 alkyl dimethicone/polycyclohexene oxide crosspolymer, C12-13 alkyl ethylhexanoate, C12-15 alkyl ethylhexanoate, C14-18 alkyl ethylhexanoate, C12-13 alkyl lactate, C12-15 alkyl lactate, C20-24 alkyl methicone, C24-28 alkyl methicone, calodendrum capense nut oil, calophyllum tacamahaca seed oil, cetearyl dimethicone/vinyl dimethicone crosspolymer, cetearyl ethylhexanoate, cetearyl isononanoate, cetearyl nonanoate, cetearyl palmitate, cetrimonium laureth-12 succinate, cetyl acetate, cetyl caprylate, cetyl C12-15 pareth-8 carboxylate, cetyl dimethicone, cetyl dimethicone/bis-vinyldimethicone crosspolymer, cetyl dimethyloctanoate, cetyl esters, cetyl ethylhexanoate, cetyl glyceryl ether, cetyl glycol, cetyl glycol isostearate, cetyl isononanoate, cetyl lactate, cetyl laurate, cetyl oleate, cetyloxy dimethicone, C12-15 pareth-3 benzoate, C12-15 pareth-9 hydrogenated tallowate, C11-15 pareth-3 oleate, C12-15 pareth-12 oleate, C11-15 pareth-3 stearate, C11-15 pareth-12 stearate, dibutyl adipate, dibutyldecyl IPDI, dibutyloctyl IPDI, dibutyloctyl malate, dibutyloctyl sebacate, dibutyl sebacate, Ddi-C12-15 alkyl adipate, di-C12-15 alkyl fumarate, di-C12-13 alkyl malate, di-C12-15 alkyl maleate, di-C12-13 alkyl tartrate, —C14-15 alkyl tartrate, dicaprylyl carbonate, dicaprylyl ether, dicaprylyl maleate, dicetyl adipate, dicocoyl pentaerythrityl distearyl citrate, diethyl adipate, isobutyl myristate, isobutyl palmitate, isobutyl pelargonate, isobutyl stearate, isobutyl tallowate, isocetyl alcohol, isocetyl ethylhexanoate, isocetyl isodecanoate, isocetyl isostearate, isocetyl laurate, isocetyl linoleoyl stearate, isocetyl palmitate, isocetyl stearate, lanolin, lanolin oil, lanolin wax, lauryl lactate, neopentyl glycol diheptanoate, neopentyl glycol diisononanoate, neopentyl glycol dilaurate, octyldodecyl ethylhexanoate, octyldodecyl lactate, octyldodecyl neodecanoate, octyldodecyl neopentanoate, PPG-3 benzyl ether myristate, PPG-1-ceteth-1, PPG-1-ceteth-5, PPG-1-ceteth-10, PPG-1-ceteth-20, sunflower oil, safflower oil, mineral oil, almond oil, and jojoba oil diisoamyl malate, diethylhexyl malate, dibutyloctyl malate, dimethyl capramide, diethylhexyl 2,6 napthalate, N,N-dimethyldesamide, diisopropyl adipate, phenethyl benzoate, octocrylene, PEG-7 methyl ester, and combinations thereof. In one aspect, PPG-3 benzyl ether myristate is used as a spreading agent. In another aspect, a carbomer is used as a gelling agent or rheology modifier.

The invention provides a method for treating aging skin by topically applying a cosmetic composition comprising umbilical cord blood serum, preferably in a cosmetically acceptable vehicle, over the affected area for a period of time sufficient to reduce, ameliorate, reverse, or prevent dermatological signs of aging. This method is particularly useful for treating signs of skin photoaging and intrinsic aging.

Generally, the improvement in the condition and/or aesthetic appearance involves the regulation of wrinkles and/or surface enhancement, such as radiance and glow. In one aspect, improvement in the condition and/or aesthetic appearance involves is selected from the group consisting of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

The composition will typically be applied to the skin one, two, or three times daily for as long as is necessary to achieve desired anti-aging results. The treatment regiment may comprise daily application for at least one week, at least two weeks, at least four weeks, at least eight weeks, or at least twelve weeks. Chronic treatment regimens are also contemplated.

A composition comprising umbilical cord blood serum is topically applied to an "individual in need thereof," by which is meant an individual that stands to benefits from reducing visible signs of skin damage or aging. In a specific embodiment, the umbilical cord blood serum is provided in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

In one embodiment, methods for treating fine lines and wrinkles comprise topically applying the inventive compositions comprising umbilical cord blood serum to the skin of an individual in need thereof, e.g., topically application directly to the fine line and/or wrinkle in an amount and for a time sufficient to reduce the severity of the fine lines and/or wrinkles or to prevent or inhibit the formation of new fine lines and/or wrinkles. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). This embodiment includes treatment of wrinkles on the skin of the hands, arms, legs, neck, chest, and face, including the forehead.

It is also contemplated that the compositions of the invention will be useful for treating thin skin by topically applying the composition to thin skin of an individual in need thereof. "Thin skin" is intended to include skin that is thinned due to chronological aging, menopause, or photo-damage. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in patients that have not manifested signs of skin aging, most commonly in individuals under 25 years of age. The method may also reverse or treat signs of aging once manifested as is common in patients over 25 years of age.

The following examples are directed to various exemplary embodiments of the skin care compositions and their use in accordance with the present invention.

Example 1

Cosmetic Composition

In this example, an exemplary cosmetic composition was prepared in accordance with the present invention. The cosmetic composition is ideally suited to be used as an anti-aging cream. Table 1 provides a list of the various ingredients.

TABLE 1

Formulation Containing Cord Serum

| Formulation Components | Range % | Phase |
|---|---|---|
| Acetyl Hexapeptide-3 (Argireline) | 0.5-1.5 | A |
| Dipeptide Tyrosil Arginine (Calmomensine, Hydroxyethylcellulose, Laureth-3 Acetyl Dipeptide, Cetyl Ester) | 2.0-3.0 | A |
| Human Umbilical Cord Serum | 0.1-0.35 | A |
| Juglans Regia leaves & shell extract, Centella leaves, Pyrus Germanica leaves, Lecithin (PHYTOTAL FM) | 3.5-5.5 | A |
| Palmitoyl Oligopeptide and Palmitoyl Tetrapeptide-7 (MATRIXL 3000) | 3.0-5.0 | A |
| Phosphatidyl choline | 0.5-1.2 | A |
| Stevia Rebaudiana Bertoni (Phytessence Stevia) | 1.0-2.5 | A |
| Undaria Pinnatifidia (Phytessence Wakami) | 2.0-4.0 | A |
| Deionized water qs | 35-45 ml | B |
| Dimethyl Isosorbide (Arlasolve DMI-PC) | 1.0-3.0 | B |
| Phenoxyethanol-SA (Sorbic acid) | 0.005-3 | B |

TABLE 1-continued

Formulation Containing Cord Serum

| Formulation Components | Range % | Phase |
|---|---|---|
| Sodium Benzoate | 0.005-3 | B |
| Potassium Sorbate | 0.005-3 | B |
| Triathanolamine | 0.75-1.5 | B |
| Hyaluronic Acid (Sodium hyaluronate) | 0.5-1.5 | C |
| Myristamidopropyl PG-Dimonium Chloride Phosphate (Arlasilk Phospholipis PTM) | 0.3-0.6 | C |
| PPG-3 Benzyl Ether Myristate (Crodamol STS) | 2.0-3.8 | C |
| Almond Oil (Cropure Almond) | 0.3-0.7 | D |
| Caprylic/Capri triglycerides (Crodamol GTCC) | 0.75-1.5 | D |
| Jojoba Oil | 0.75-1.5 | D |
| Carbomer 924 (Optasense G-34) | 0.75-1.5 | D |

The components of Part A were mixed together and heated to about 70 to 80° C. The mixture was allowed to cool to about 50° C. The Part A mixture was then homogenized at increasing rates. In this example, the mixtures was homogenized for about 60 seconds at about 11,000 rpm, about 60 seconds at about 13,000 rpm, about 60 seconds at about 19,000 rpm, about 60 seconds at about 22,000 rpm, and about 60 seconds at about 24,000 rpm.

Separately, the components of Part B were mixed together and heated to about 70 to 80° C. After cooling to about 50° C., the mixture from part A was added to Part B with continuous mixing. The Part A/B mixture was then allowed to cool to about 40° C.

Separately, the components of Part C were mixed together with sufficient deionized water to solubilize the components of Part C.

Lastly, the Part A/B mixture, Part C mixture, and Part D components were all mixed together at about 75 to 80° C. The mixing was continued to provide a uniform texture as the product cooled: In the laboratory, an IKA Turrax homogenizer T-25 Basic S1 equipped with an IKA S25N-10G dispersing tool was used. The dispersing tool is immersed in the completed formula, and the homogenizer is operated for about 5 to 8 minutes at about 24,000 rpm. The intense shearing reduces particles size to about 50 to 1000 nanometers.

Example 2

Histogeometric Analysis

This example was designed to test the effects that the topical cream containing cord serum of Example 1 had on human skin. As a control, the topical cream minus the cord serum was also evaluated and both products were compared with an untreated site.

Methods

Six healthy volunteers were enrolled in the study. Product A was applied to the right aspect of the upper inner arm (R site), product B was applied to the left aspect of the upper inner arm (L site) and the volar forearm was chosen as the untreated site. Both products were applied daily for 26 days. The volar forearm received no product but was rubbed gently, daily, in an effort to simulate the manner in which both products were applied to the skin.

At the end of the treatment period, a 2-3 mm punch biopsy specimen was obtained from each treated site and the untreated site. Each specimen was immediately placed in 10% buffered formalin and processed for paraffin sectioning. All sections were five-micrometers in thickness and all slides were stained simultaneously as a group for each histochemical determination. The entire biopsy specimen was photographed with a high resolution digital camera system (Axiocam, Zeiss Corporation) mounted on a Zeiss Axioplan 2 light microscope at a magnification of 20×. All slides were photographed under the identical white balance light settings and exposure time to insure consistency in micrographs. Micrographs were subsequently analyzed using computer assisted image analysis software (Axiovision, Zeiss Corporation). All measurements were made from at least four areas of the biopsy specimen, except for two biopsies, which had smaller amounts of tissues and thus three measurements were made.

Five-micrometer paraffin sections were stained with hematoxylin-eosin ("H&E") for overall morphologic evaluation and viable epidermal thickness determinations (VET; Table 2). For estimation of viable epidermal thickness, care was taken to cut the sections perpendicular to the surface. The VET includes the area from the dermoepidermal interface to the lowermost portion of the stratum corneum. For estimation of elastic fibers, van Geison's stain was employed, which stains elastic fibers blue-black to black, collagen pale red, other tissue elements yellow, and nuclei blue to black. For pro-collagen, anti-type I collagen (EMD Bioscience Inc.) antibody was used. This antibody to type I collagen was made against the triple helical portion and it is able to stain procollagen I. Immunohistochemical analysis of the paraffin sections was carried out using the DAB kit, which produces a brown reaction product. For glycosaminoglycans ("GAGs"), Hale's colloidal iron was used since Hale's stainable material (blue) represents, for the most part, GAGs and is commonly used as an indicator of changes in ground substance.

The quantification of stainable material was determined using a custom designed software program, integrated into the Axiovision image analysis system (Zeiss Corporation). The analysis is conducted in the following manner: (i) the reaction product (i.e., blue-black—elastin; brown—pro-collagen; blue—GAGs) is detected from a histogram and only objects with that color are outlined on the micrograph. The total area occupied by the outlined areas is measured; (ii) the entire area of the dermis is outlined and measured; and (iii) area of reaction product divided by total area=the percentage of material deposited.

It should be noted that all photomicrographs were taken and analyses performed in a double blind manner, and only after the data was tabulated was the investigator informed about the identity of the R and L sites.

Results

Morphology

The epidermis did not appear to be morphologically altered in any of the subjects at the two treatment as well as the untreated site. In most instances, the undulating nature of the dermoepidermal interface was maintained. The granular layer was prominent in all specimens and there was little evidence of apoptosis (sunburn cells) within the epidermis. The "basketweave" architecture of the stratum cornea, characteristic of formalin-fixed human skin was maintained in all subjects in all sites.

For the most part, the fibrous components of the dermis (i.e., collagen, elastin) did not appear altered on the H&E sections from any of the treatment regimens or the untreated sites of the six subjects. In some cases, the dermis from the untreated site appeared more compact. In a few subjects, occasional areas of blue-gray staining material, usually associated with elastosis, were noted; however, frank signs of photodamage were not seen in any of the subjects. Importantly, there did not appear to be an unusual amount of inflammatory cells in biopsies from any of the treatment sites or in the untreated site from any of the subjects. Some increased cellularity was noted around portions of hair follicles present in some of the sections but this was not deemed significant. Vascular profiles appeared normal and there was no evidence of increased vascularity, vasodilatation and/or extravasation of red blood cells.

Viable Epidermal Thickness (VET)

There was no consistent trend seen in the VET measurements (Tables 2 and 3). Subjects 1, 2, and 6 had similar VET values for the untreated, R and L sites. Subject 3 had a thinner VET measurement for the untreated site compared with the R and L sites. Subject 4 had a thinner VET for the R site compared with the untreated and L site, whereas Subject 5 had a thinner VET for the L site when compared with the R and untreated sites. Given the lack of inflammation, which usually is responsible for epidermal thickening, it is not surprising that VET was not affected by either R or L treatment.

Elastin

The overall area of the dermis occupied by elastin appeared to be greater in the untreated sites from all six subjects when compared with either the R or L treatment site (Tables 2 and 3). This finding in no way implies that either of the treatments had a negative impact on elastin fiber deposition, synthesis, and/or destruction. It most likely represents inherent differences in elastin content between the volar forearm and the upper inner arm.

With respect to treatment sites, there was no obvious trend (Tables 2 and 3). Subjects 1 and 4 had significantly more elastin-stained material in the L site when compared with the R site. In contrast, subject 3 had significantly more elastin-stained material in the R site compared with the L site. There was no significant difference in elastin-stained material when the R and L sites were compared in Subjects 2, 5, and 6. When all six subjects were compared there was no change in elastin-stained material (Table 2). This is not surprising since elastin is one of the more stable components of the dermis with an extremely long turnover time. New elastin deposition is most often seen during tissue regeneration following a wound. Thus the lack of evidence for skin perturbation due to either of the treatments could account for the failure to detect a change in elastin.

Procollagen

Five of the six subjects showed an increase in the immunostaining for procollagen when the R site was compared with the L site (Tables 2 and 3). Of these 5 subjects, one (#4) was significant at the $P<0.05$ level and two (#2 and #3) were highly significant ($P<0.01$ level). While an overall increase in procollagen immunostained material was detected for the R site versus the L site in Subjects 1 and 5, the difference was not statistically significant. The R and L treatment did not affect the procollagen-stainable material in Subject 6. When all six subjects were combined there was a greater amount of immunostaining for procollagen in the R site versus the L site; however due to subject to subject variability, this difference was not significant.

With respect to the untreated site, 4 subjects had less immunostained material corresponding to procollagen when compared with the R site; two subjects had more immunostained material. Due to potential differences in the dermis between the treated and untreated sites it is difficult to meaningfully interpret these changes.

GAGs

Four of the six subjects had significantly ($P<0.01$) increased Hale's-stainable material in the R site when compared with the L site (Tables 2 and 3). Subjects 4 and 6 had increases in Hale's-stainable material in the L site versus the R site; however, this difference was not statistically significant. When all six subjects were combined there was a greater amount of Hale's stainable material in the R site versus the L site; however due to subject to subject variability, this difference was not significant.

The untreated site showed the greatest subject to subject variability in Hale's-stainable material. Nevertheless 4 subjects had greater Hale's-stainable material in the R site when compared to the untreated site. As mentioned previously, due to regional differences it is difficult to draw meaningful comparisons between the treated and untreated sites.

GAG-induced changes because collagen fibers are a more stabile dermal component than GAGs. Taken together these findings suggest that facial cream with serum cord complex stimulates the synthesis of GAGs and procollagen, which in part is responsible for the clinical changes seen after use of this product.

TABLE 2

| Histogeometric Analyses | | | | | | | |
|---|---|---|---|---|---|---|---|
| | 1 | 2 | 3 | 4 | 5 | 6 | Σ |
| VET (microns) | | | | | | | |
| NT | 126 ± 7 | 99 ± 7 | 98 ± 8 | 115 ± 4 | 128 ± 16 | 114 ± 3 | 113 ± 12 |
| R | 132 ± 7 | 94 ± 4 | 120 ± 15 | 91 ± 2 | 118 ± 20 | 119 ± 3 | 96 ± 37 |
| L | 126 ± 5 | 91 ± 8 | 115 ± 10 | 108 ± 4 | 87 ± 9 | 113 ± 5 | 107 ± 14 |
| Elastin (% dermis) | | | | | | | |
| NT | 14.0 ± 1 | 10.4 ± 1.1 | 12.5 ± 0.7 | 12.2 ± 2.4 | 13.0 ± 2.0 | 7.6 ± 2.0 | 11.6 ± 2.0 |
| R | 8.0 ± 1.5 | 9.8 ± 0.3 | 8.3 ± 1.6** | 5.8 ± 0.4 | 8.2 ± 1.1 | 5.0 ± 0.4 | 7.5 ± 1.6 |
| L | 11.8 ± 0.7** | 8.0 ± 1.7 | 3.3 ± 0.3 | 8.6 ± 0.8** | 9.5 ± 1.1 | 5.3 ± 1.1 | 7.8 ± 2.8 |
| Procollagen (% upper dermis) | | | | | | | |
| NT | 8.1 ± 0.6 | 9.9 ± 1.7 | 4.7 ± 1.8 | 16.2 ± 1.8 | 9.1 ± 1.5 | 16.4 ± 2.9 | 10.7 ± 4.3 |
| R | 9.2 ± 0.6 | 13.3 ± 1.6** | 9.9 ± 1.7** | 12.3 ± 2.3* | 19.2 ± 5.4 | 10.0 ± 2.4 | 12.3 ± 3.4 |
| L | 9.1 ± 1.1 | 7.8 ± 1.3 | 5.2 ± 2.1 | 7.9 ± 1.8 | 15.8 ± 3.4 | 11.5 ± 1.4 | 9.6 ± 3.4 |
| GAGs (% dermis) | | | | | | | |
| NT | 1.8 ± 0.8 | 24.3 ± 2.8 | 22.6 ± 2.4 | 13 ± 3.8 | 14.7 ± 2.2 | 5.2 ± 0.9 | 13.6 ± 8 |
| R | 22 ± 5.0** | 11.4 ± 0.9** | 20.1 ± 2.2** | 15 ± 2.7 | 23 ± 3.0** | 10.8 ± 3.9 | 17.4 ± 4.9 |
| L | 4.4 ± 2.3 | 6.5 ± 1.5 | 8.3 ± 2.7 | 18 ± 5.5 | 14.3 ± 1.5 | 13.9 ± 3.9 | 10.9 ± 4.8 |

*P < 0.05; **P < 0.01

CONCLUSIONS

There are several conclusions to be drawn from this small pilot study. The active and vehicle-only formulations did not have any deleterious effects on the skin that were discernable at the light microscopic level. This is important because any changes seen in the other parameters were not confounded by and/or secondary to an inflammatory response. The assumption is that any changes are the result of the cord serum complex. The R site, which received the cord serum complex daily for 26 days, had increased amounts of stained material corresponding to procollagen and GAGs compared to the vehicle-treated (L) site. Cord serum complex had no discernable effect on VET or elastin.

Since ground substance (GAGs) is the dermal component that is most rapidly turned over, it is not surprising that changes were seen. Furthermore, ground substance is well known for its water-holding capacity, and it is this increase in water binding that could be partially responsible for the disappearance of fine-line wrinkling after use of this product. The increase in procollagen-stained material was also significant. In contrast to the GAGs, collagen is slowly turned over. This suggests that some of the changes in skin quality that have been reported following use of the cord serum complex facial cream may be somewhat more long lasting than the

TABLE 3

| | Percentage Change | | | | | |
|---|---|---|---|---|---|---|
| | 1 | 2 | 3 | 4 | 5 | 6 |
| VET | | | | | | |
| R vs L | 4.5↑ | 3↑ | 4.2↑ | 15.7↓ | 26.3↑ | 5.0↑ |
| R vs NT | 4.5↑ | 5.1↓ | 18.3↑ | 20.8↓ | 7.8↓ | 4.2↓ |
| L vs NT | 0 | 8.1↓ | 14.8↑ | 6.1↓ | 32.0↓ | 0.9↓ |
| elastin | | | | | | |
| R vs L | 32.2↓ | 18.4↑ | 60.2↑ | 32.6↓ | 13.7↓ | 5.7↓ |
| R vs NT | 42.9↓ | 5.8↓ | 33.6↓ | 52.5↓ | 36.9↓ | 34.2↓ |
| L vs NT | 15.7↓ | 23.1↓ | 73.6↓ | 29.5↓ | 26.9↓ | 30.3↓ |
| procollagen | | | | | | |
| R vs L | 1.1↑ | 41.4↑ | 47.5↑ | 35.8↑ | 17.7↑ | 13.0↓ |
| R vs NT | 12.0↑ | 25.6↑ | 52.5↑ | 24.0↓ | 52.6↑ | 39.0↓ |
| L vs NT | 11.0↑ | 21.2↓ | 9.6↑ | 51.2↓ | 42.4↑ | 6.1↓ |
| GAGs | | | | | | |
| R vs L | 80.0↑ | 43.0↑ | 58.7↑ | 16.7↓ | 37.8↑ | 22.3↑ |
| R vs NT | 91.8↑ | 53.1↓ | 11.1↓ | 13.3↑ | 36.0↑ | 51.9↑ |
| L vs NT | 59.0↑ | 73.3↓ | 63.3↓ | 27.8↑ | 2.7↓ | 62.6↑ |

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A skin care composition for topical application to the human skin comprising an effective amount of umbilical cord blood serum wherein the cells have been removed so the umbilical cord serum is substantially free of whole cells, and further comprising a peptide selected from the group consisting of tyr-arg, acetyl hexapeptide-3, palmitoyl oligopeptide, palmitoyl tetrapeptide-7, and mixtures thereof.

2. A skin care composition for topical application to the human skin comprising an effective amount of umbilical cord blood serum wherein the cells have been removed so the umbilical cord serum is substantially free of whole cells, further comprising a biological additive selected from the group consisting of *Juglans regia, Centella asiatica, Pyrus germanica* extract, and mixtures thereof.

3. A skin care composition for topical application to the human skin comprising an effective amount of umbilical cord blood serum wherein the cells have been removed so the umbilical cord serum is substantially free of whole cells, further comprising a biological additive selected from the group consisting of *Undaria pinnatifida* and *Stevia rebaudiana* Bertoni, and mixtures thereof.

4. A skin care composition for topical application to the human skin comprising an effective amount of umbilical cord blood serum wherein the cells have been removed so the umbilical cord serum is substantially free of whole cells, further comprising a preservative selected from the group consisting of one or more parabens.

5. A skin care composition for topical application to the human skin comprising an effective amount of umbilical cord blood serum wherein the cells have been removed so the umbilical cord serum is substantially free of whole cells, further comprising a penetration enhancer selected from the group consisting of dimethyl isosorbide and diethyl-glycol-monoethylether.

6. A skin care composition for topical application to the human skin comprising an effective amount of umbilical cord blood serum wherein the cells have been removed so the umbilical cord serum is substantially free of whole cells, further comprising one or more skin-conditioning emollients selected from the group jojoba oil, almond oil, capric/caprylic triglyceride and mixtures thereof.

7. A skin care composition for topical application to the human skin comprising about 0.1 wt % to about 0.35 wt % umbilical cord blood serum wherein the cells have been removed so the umbilical cord serum is substantially free of whole cells, about 3 wt % to 5 wt % palmitoyl oligopeptide, about 3 wt % to about 5 wt % palmitoyl tetrapeptide-7.

8. The skin care composition of claim 7 further comprising about 2 wt % to about 3 wt % of the dipeptide tyr-arg and about 0.5 wt % to 1.5 wt % acetyl hexapeptide-3.

9. The skin care composition of claim 8 further comprising about 0.5 wt % to about 1.2 wt % phosphatidyl choline, about 0.5 wt % to about 1.5 wt % hyaluronans, and 0.01 wt % to 0.085 wt % of a preservative selected from the group consisting of methyl paraben and propyl paraben, or mixtures thereof.

10. The skin care composition of claim 9 further comprising *Juglans regia, Centella asiatica, Pyrus germanica, Undaria pinnatifida*, and *Stevia rebaudiana* Bertoni.

* * * * *